US012642506B2

(12) United States Patent
Wenzel et al.

(10) Patent No.: US 12,642,506 B2
(45) Date of Patent: Jun. 2, 2026

(54) PRESET OPTIMIZATION QUICK GUIDE FOR IMPROVED IMAGE QUALITY

(71) Applicant: GE Precision Healthcare LLC, Waukesha, WI (US)

(72) Inventors: Timo Wenzel, Vocklamarkt (AT); David Puhringer, Piberbach (AT)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/633,177

(22) Filed: Apr. 11, 2024

(65) Prior Publication Data

US 2025/0318807 A1    Oct. 16, 2025

(51) Int. Cl.
*A61B 8/00* (2006.01)

(52) U.S. Cl.
CPC ............ *A61B 8/467* (2013.01); *A61B 8/4444* (2013.01); *A61B 8/465* (2013.01)

(58) Field of Classification Search
CPC ........ A61B 8/467; A61B 8/4444; A61B 8/465
See application file for complete search history.

(56) References Cited

U.S. PATENT DOCUMENTS 5,897,503 A  *  4/1999  Lyon ........................ A61B 8/00
                                              600/459
6,516,215 B1    2/2003  Roundhill 8,038,619 B2 *  10/2011  Steinbacher ........... A61B 8/467
                                              600/459
11,478,223 B2  10/2022  Tashiro
11,523,803 B2  12/2022  Borreani et al.
11,564,861 B1 *  1/2023  Gaines ................... A61H 23/04
2004/0015080 A1 *  1/2004  Kelly ..................... A61B 8/406
                                              600/459
2007/0122021 A1 *  5/2007  Zingaretti ............. G06T 7/0014
                                              382/132
2008/0247618 A1 *  10/2008  Laine .................... G06T 7/0012
                                              382/128
2009/0012401 A1 *  1/2009  Steinbacher ........... A61B 8/467
                                              600/459
2010/0249598 A1 *  9/2010  Smith .................. A61B 8/4455
                                              600/459

(Continued)

*Primary Examiner* — Sanjay Cattungal
(74) *Attorney, Agent, or Firm* — McAndrews, Held & Malloy, Ltd.; Daniel Bissing; David Bates

(57) ABSTRACT

Systems and methods for performing an ultrasound image acquisition using an ultrasound probe include performing an ultrasound image acquisition using an ultrasound probe, activating, by at least one processor, a user interface, presenting, by the at least one processor, via the user interface, one or more image quality characteristics for the ultrasound image acquisition, receiving feedback, by the at least one processor, for adjusting an image quality characteristic of the one or more image quality characteristics, wherein the image quality characteristic comprises one or more image quality parameters, adapting, by the at least one processor, the ultrasound image acquisition based on the feedback, to adjust the image quality characteristic and produce an adapted ultrasound image acquisition by modifying the one or more image quality parameters, and presenting, by the at least one processor, the ultrasound image acquisition and the adapted ultrasound image acquisition via the user interface.

22 Claims, 10 Drawing Sheets

(56)                 References Cited

U.S. PATENT DOCUMENTS

| | | | | |
|---|---|---|---|---|
| 2010/0324423 A1* | 12/2010 | El-Aklouk | ........... | A61B 8/4488 |
| | | | | 600/444 |
| 2011/0074244 A1* | 3/2011 | Osawa | ................. | B06B 1/0622 |
| | | | | 310/318 |
| 2011/0082369 A1* | 4/2011 | Mohr | ..................... | A61B 1/043 |
| | | | | 600/431 |
| 2011/0087107 A1* | 4/2011 | Lindekugel | .......... | A61B 8/4455 |
| | | | | 600/459 |
| 2011/0313293 A1* | 12/2011 | Lindekugel | ............ | A61B 10/00 |
| | | | | 600/459 |
| 2012/0165679 A1* | 6/2012 | Orome | ............. | A61B 5/150748 |
| | | | | 600/461 |
| 2012/0179044 A1* | 7/2012 | Chiang | .................... | A61B 8/14 |
| | | | | 600/467 |
| 2012/0289836 A1* | 11/2012 | Ukimura | ................. | A61B 8/14 |
| | | | | 600/463 |
| 2013/0338503 A1* | 12/2013 | Cohen | ................. | A61B 8/4411 |
| | | | | 600/443 |
| 2013/0338508 A1* | 12/2013 | Nakamura | ........... | A61B 8/4494 |
| | | | | 600/459 |
| 2014/0031694 A1* | 1/2014 | Solek | ................... | A61B 8/4427 |
| | | | | 600/459 |
| 2014/0066779 A1* | 3/2014 | Nakanishi | ............ | A61B 8/4444 |
| | | | | 600/459 |
| 2014/0180116 A1* | 6/2014 | Lindekugel | .......... | A61B 8/4455 |
| | | | | 600/459 |
| 2014/0276069 A1* | 9/2014 | Amble | ................. | A61B 8/4488 |
| | | | | 600/447 |
| 2014/0376793 A1* | 12/2014 | Lee | ........................ | G16H 50/20 |
| | | | | 382/131 |
| 2015/0359520 A1* | 12/2015 | Shan | .................... | A61B 8/0858 |
| | | | | 600/443 |
| 2016/0026894 A1* | 1/2016 | Nagase | .................. | A61B 8/463 |
| | | | | 600/443 |
| 2017/0328751 A1* | 11/2017 | Lemke | ..................... | G01H 9/00 |
| 2019/0216440 A1 | 7/2019 | Kimoto et al. | | |
| 2020/0163654 A1* | 5/2020 | Satir | ........................ | A61B 8/58 |
| 2021/0059639 A1* | 3/2021 | Howell | ................ | A61B 8/4444 |
| 2021/0212668 A1* | 7/2021 | Li | ........................... | G01S 17/66 |
| 2022/0071593 A1* | 3/2022 | Tran | ....................... | A61B 8/463 |

* cited by examiner

PRESET OPTIMIZATION QUICK GUIDE FOR IMPROVED IMAGE QUALITY

FIELD

Certain embodiments relate to ultrasound imaging. More specifically, certain embodiments relate to a preset optimization quick guide for efficiently configuring and/or adjusting ultrasound images for improved image quality.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a powerful tool for visualization. Ultrasound images are acquired by an ultrasound probe that may be used to scan anatomical structures to produce ultrasound images. However, current methods and ultrasound systems for configuring and/or optimizing ultrasound images may be inefficient and/or require a user to have a high level of technical knowledge.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for providing a preset optimization quick guide for improved image quality, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
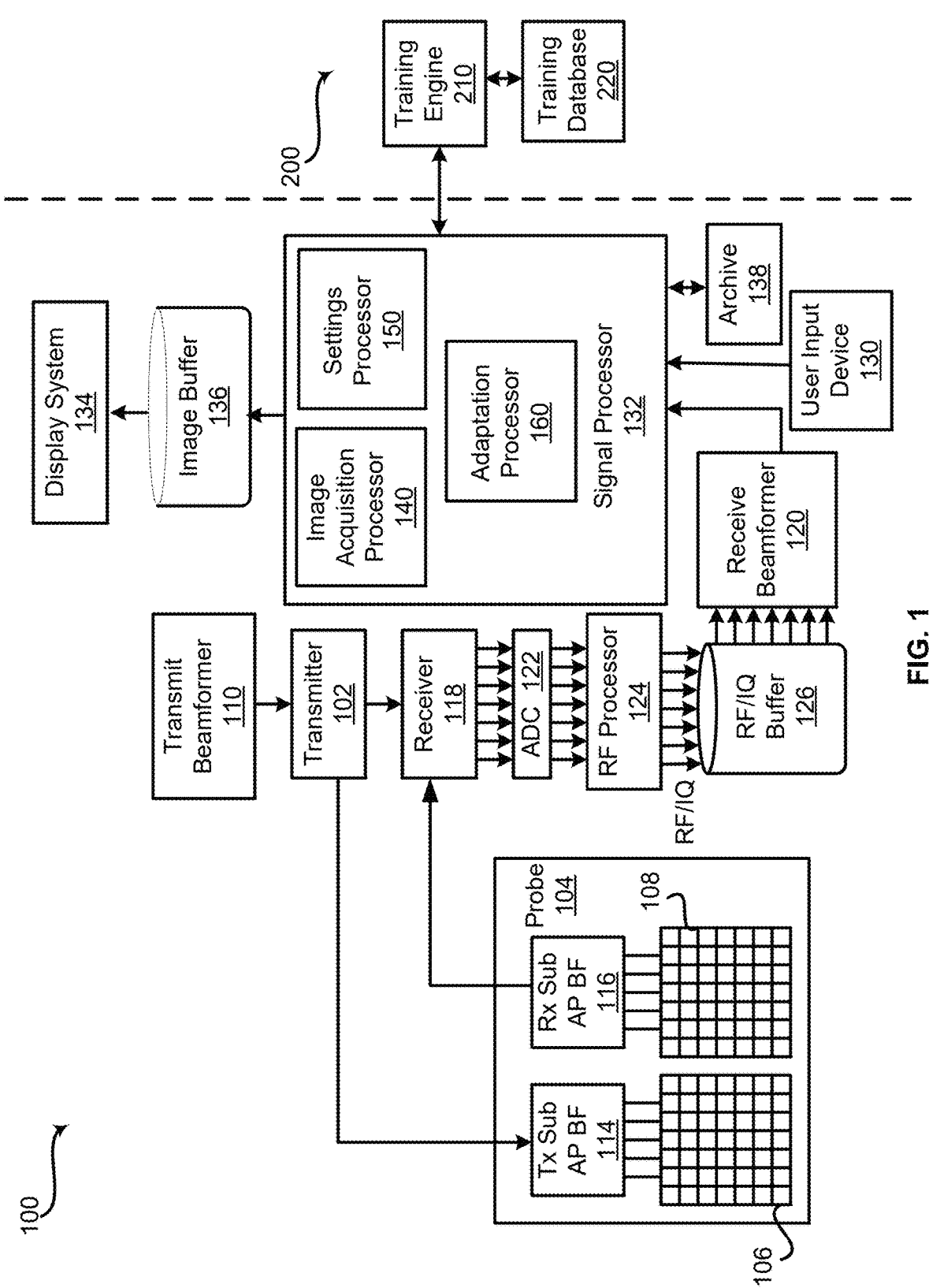
FIG. 1 is a block diagram of an exemplary ultrasound system that is operable to obtain ultrasound images with a preset optimization quick guide, in accordance with various embodiments.

Certain embodiments may be found in a method and system for providing a preset optimization quick guide for efficiently configuring and/or adjusting ultrasound images for improved image quality. Aspects of the present disclosure have the technical effect of providing ultrasound images with improved quality by using a preset optimization quick guide. Various embodiments have the technical effect of aiding a user in configuring an ultrasound system for first use and/or when the ultrasound system settings are being modified. Certain embodiments have the technical effect of modifying ultrasound image settings for different types of ultrasounds and/or for obtaining improved ultrasound images. Certain embodiments have the technical effect of providing a preset optimization guide for improving the appearance of ultrasound images.

Certain embodiments have the technical effect of improving the quality of ultrasound images by adjusting image parameters and/or image characteristics of ultrasound images. Various embodiments have the technical effect of providing increased clarity and details in ultrasound images in live ultrasound images, thereby aiding in diagnosis using ultrasound images and decreasing ultrasound scanning time for patients in many situations.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and the like. The term, "ultrasound image," as used herein, is used to refer to ultrasound image and/or ultrasound image volumes, such as a bi-plane image, a single 2D image, a rendering of a volume (3D/4D), 2D bi-plane image slices extracted from a volume (3D/4D), and/or any suitable ultrasound image. In some examples, the ultrasound image may be a still image or an ultrasound clip. For purposes of this disclosure, the term "still image" may be used to refer to a single ultrasound frame, while the term "ultrasound clip" may be used to refer to a plurality of ultrasound frames acquired in sequence, each at a different point in time. When displayed, each of the ultrasound frames in an ultrasound clip is displayed in sequence, which allows the ultrasound clip to display motion in a manner similar to a movie. The ultrasound clip, which is also commonly referred to as a cine loop by those skilled in the art, may include either 2D or 3D ultrasound frames acquired over a period of time. In some examples, the ultrasound images and/or ultrasound clips may be displayed in real-time and/or may be stored in a computer readable medium for later retrieval.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to obtain an ultrasound volume from bi-plane ultrasound scanning. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may comprise a two-dimensional (2D) array of piezoelectric elements. In various embodiments, the ultrasound probe 104 may be a matrix array transducer or any suitable transducer operable to acquire 2D and/or 3D ultrasound image datasets. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as an abdomen, a heart, a fetus, a lung, a blood vessel, or any suitable anatomical structure(s). The ultrasound probe 104 may be a curvilinear, convex, or phased array probe, as non-limiting examples.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces, and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select displacement parameters to acquire displacements in one more directions and/or rotational displacements, manipulate the acquired 3D volume, and the like. In an exemplary embodiment, the user input device 130 may be operable to configure, manage, and/or control operation of one or more components and/or modules in the ultrasound system 100. In this regard, the user input device 130 may be operable to configure, manage, and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), a remote archive, or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image acquisition processor 140, a settings processor 150, and an adaptation processor 160. The signal processor 132 may be capable of receiving input information from a user input device 130 and/or archive 138, generating an output displayable by a display system 134, and manipulating the output in response to input information from a user input device 130, among other things. The signal processor 132, image acquisition processor 140, settings processor 150, and adaptation processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image acquisition processor 140 that comprises suitable logic, circuitry, interfaces, and/or code that may be operable to acquire ultrasound images of anatomical structures such as cardiac structures, gastroenterological structures, urological structures, reproductive structures, cardiac structures, pulmonary structures, and/or any suitable anatomical structures. The ultrasound images may be ultrasound images and/or ultrasound image volumes, such as a bi-plane image, a single 2D image, a rendering of a volume (3D/4D), 2D bi-plane image slices extracted from a volume (3D/4D), and/or any suitable ultrasound images. In some examples, the ultrasound images are still images and/or ultrasound clips. In some examples, the ultrasound images are acquired and displayed live for viewing on a display 134.

In an exemplary embodiment, the image acquisition processor 140 may acquire ultrasound images of an anatomical structure using an ultrasound probe 104. In some examples, the image acquisition processor 140 may capture and/or display ultrasound images to a user on a display system 134. In some examples, the image acquisition processor 140 may display the ultrasound images according to default settings and/or preconfigured settings. In some examples, the default and/or preconfigured settings may be provided by a settings processor 150 or an adaptation processor 160. The settings may include ultrasound acquisition settings such as image parameters, image characteristics, anatomical structures, etc., as non-limiting examples. In some examples, the image acquisition processor 140 may display the ultrasound images in real-time (e.g., live view) and/or store the ultrasound images in the archive 138 and/or any suitable data storage medium.

Figure 2:
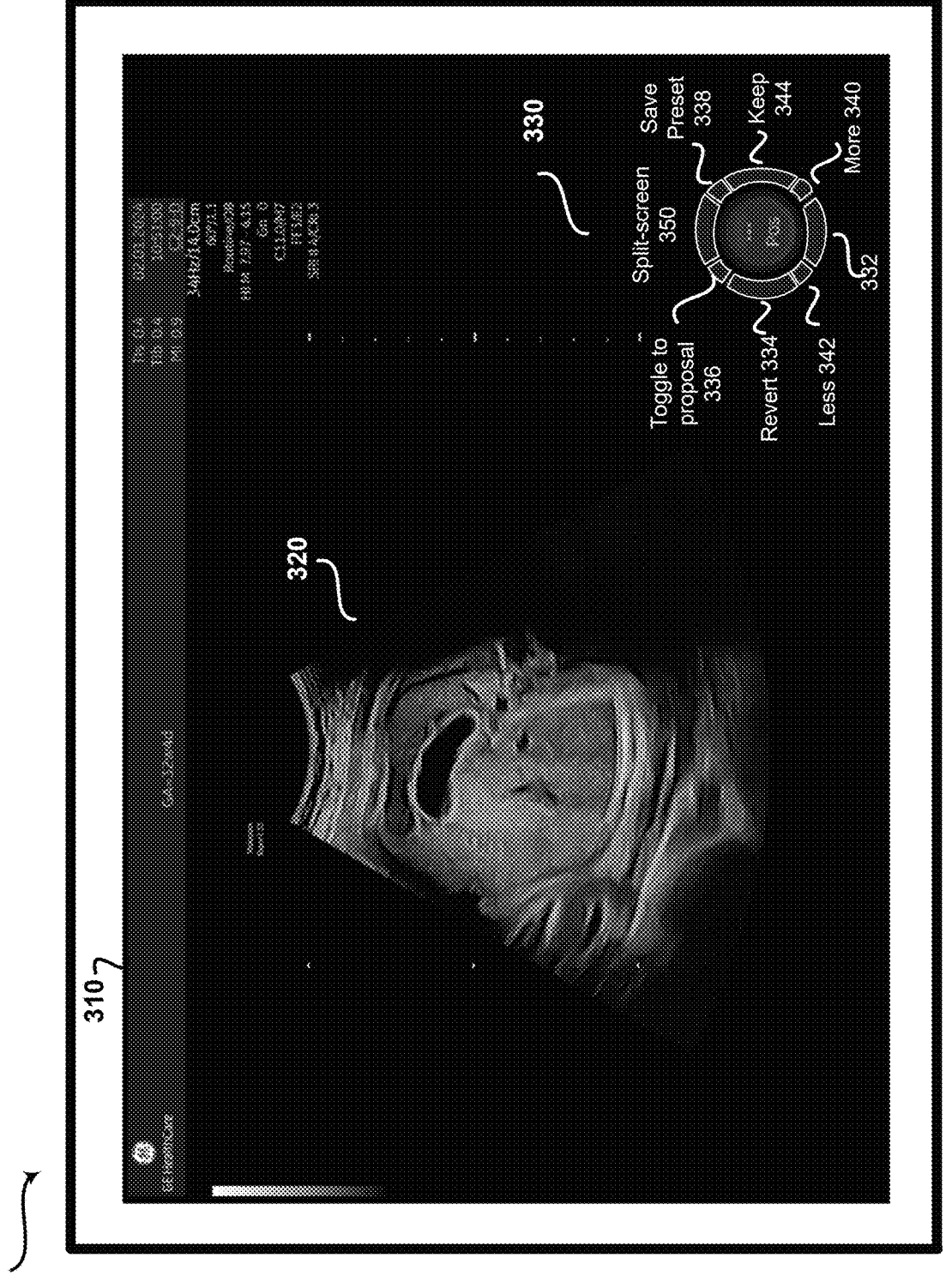
FIG. 2 is an exemplary display of an ultrasound image, in accordance with various embodiments.

FIG. 2 provides a display 300 including a user interface 310, an ultrasound image 320, and a configuration tool 330. The user interface 310 may include the ultrasound image 320 and the configuration tool 330. In some examples, the configuration tool 330 may be a separate user interface 310 on the display 300 and/or may be a separate input device. The user interface 310 may be activated and/or generated by the acquisition processor 140. The ultrasound image 320 may be acquired by the ultrasound probe 104 and positioned on the user interface 310 along with the configuration tool 330.

The configuration tool 330 may be a knob, a dial, a trackball configuration, and/or another type of user interface. In some examples, the configuration tool 330 may include graphical buttons 332 or other icons representing different functionalities in order for a user to provide input for settings related to the ultrasound image 320. For example, the graphical buttons 332 may represent functionalities such as reverting 334 back to a previous ultrasound image, toggling 336 between the ultrasound image 330 and an ultrasound image with adapted settings, increasing and/or decreasing settings (e.g. more 340, less 342) related to the ultrasound image 330, keeping 344 changes made to the settings, providing a split-screen view 350 or side-by-side display depicting both the original ultrasound image and the ultrasound image with updated settings, saving 338 current settings as preset settings, and other functional graphical buttons, as non-limiting examples.

Additionally and/or alternatively, the configuration tool 330 may be utilized to configure and/or adjust settings related to the ultrasound image 330, to retrieve settings, and to save the settings in the archive 138 and/or any other suitable data storage medium as preset settings. In some examples, the settings may be stored with a label representative of an anatomical structure, such as, kidney, cardiac, other anatomical structures, and/or other customized labels so that a user can quickly and efficiently retrieve preset image quality settings, such as image quality parameters and/or characteristics, or other settings that have been configured and saved. In some examples, the ultrasound system 100 may include default settings, image quality parameters, and/or image characteristics which may be updated and/or modified by the configuration tool 330.

Figure 3:
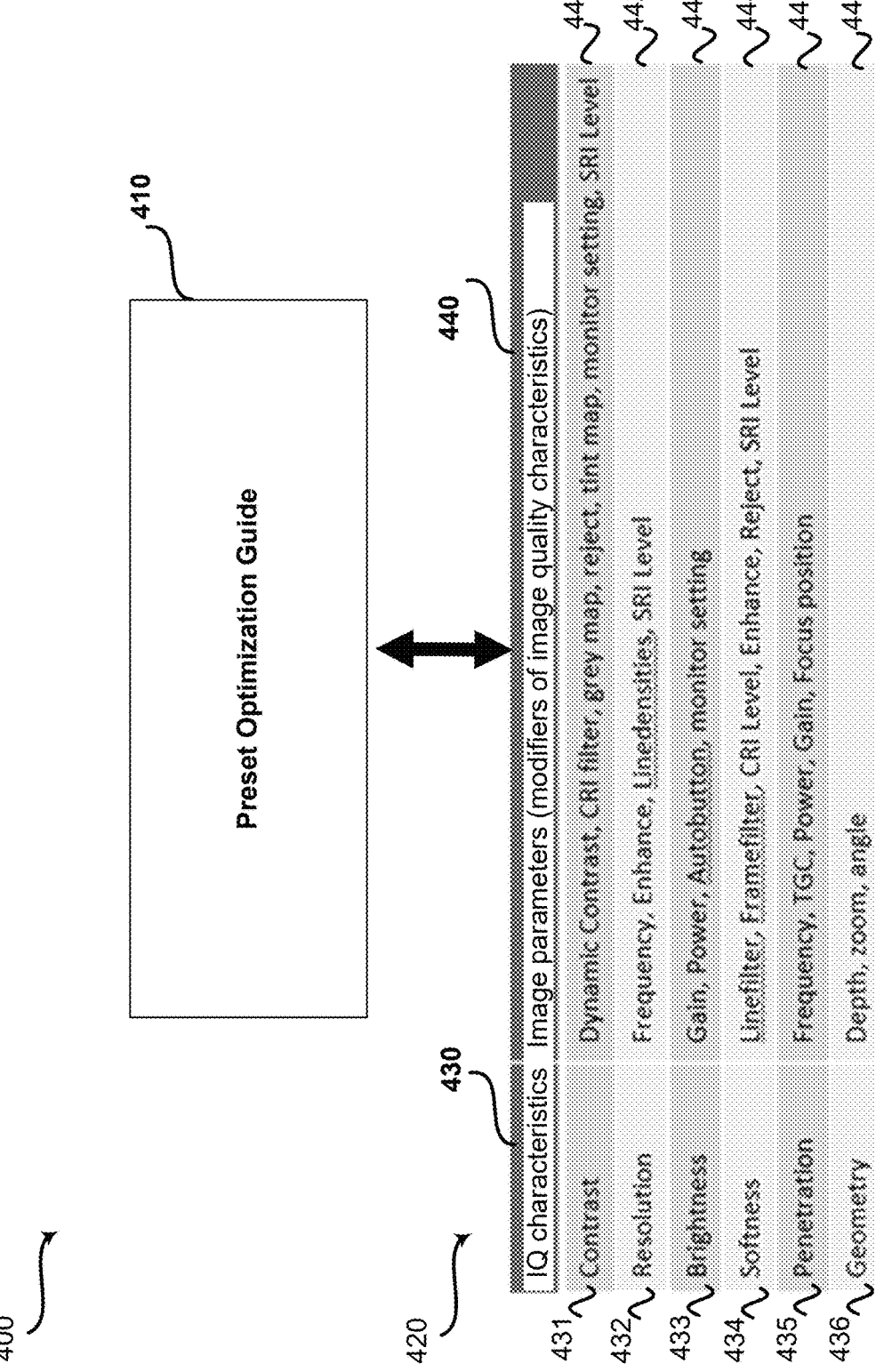
FIG. 3 is an example illustration including a preset optimization guide and a table of exemplary image quality characteristics and image parameters.

FIG. 3 is an example illustration 400 including a preset optimization guide 410 and a table 420 of exemplary settings, including exemplary image quality characteristics 430 and exemplary image parameters 440 that may be adapted based on a preset optimization guide 410. The preset optimization guide 410 may be provided by the settings processor 150 as a user interface that allows a user to input, update, and/or modify image quality characteristics 430 and/or image parameters 440. In some examples, the preset optimization guide 410 may include a configuration tool, menus, sub-menus, and/or other user interfaces that provide guidance or information to a user regarding image quality settings and/or allow a user to input, update, and/or modify image quality characteristics 430 and/or image parameters 440. In some examples, the preset optimization guide 410 may present different configuration tools, menus, sub-menus, and/or user interfaces depending on the ultrasound mode being used. For example, the preset optimization guide 410 may present different image quality characteristics, and/or different user parameters to modify the image quality characteristics based on the ultrasound mode being used, which are described above and below with relation to FIGS. 6-9.

The preset optimization guide 410 may present a user with a question or series of questions related to image quality and/or image appearance. For example, the preset optimization guide may present the user with questions such as, "Do you prefer a higher contrast image?", "Do you prefer a darker image?", "Do you prefer a brighter image?", "Do you prefer a higher axial resolution?", etc., as non-limiting examples. The preset optimization guide may also ask questions in the alternative. For example, the preset optimization guide may ask questions such as, "Would like you like a brighter or darker image?", "Would you like a lower contrast or higher contrast image?", etc.

The answers provided by the user may be used in order to configure adapted image parameters 440 for the ultrasound image, which the image acquisition processor 140 and/or the adaptation processor 160 may use in order to obtain and/or display ultrasound images. Additionally and/or alternatively, the answers provided by the user may be saved as preset settings in an archive and/or other suitable computer readable storage medium.

In some examples, the preset optimization guide 410 may provide the user information regarding each of the image quality settings such as the settings provided in table 420. In some examples, the settings information may include information regarding the image quality characteristics, the image parameters, other settings, etc. The information provided to the user may be information regarding the functionality of user parameters so that users may customize the user parameters based on the effects that each of the parameters has on the ultrasound image. For example, the preset optimization guide 410 may present information regarding contrast, brightness, etc., in the same user interface as the preset optimization guide 410, in a separate user interface, as a pop-up, or any other suitable display method.

The table 420 of settings includes image quality (IQ) parameters 430 which are made up of a combination of various adapted image parameters 440, which are modifiers of the image quality characteristics 430. The image quality characteristics 430 may be adapted based on the answers provided by the user via the preset optimization guide 410. Image quality characteristics 430 may be related to the appearance and/or quality of ultrasound images captured, such as contrast, resolution, brightness, softness, penetration, geometry, etc. Each of the image quality characteristics may be made up of one or more image parameters. In some examples, the image quality characteristics are made up of a variety of image parameters that produce an improved or customized image quality and/or appearance. In some examples, different image quality characteristics may include one or more of the same image parameters. In some examples, a combination of image parameters may be modified for each of the image quality characteristics (i.e. adapted user parameters). In some examples, the image quality characteristics 430 and/or the image parameters 440 used by the preset optimization guide 410 are based on the ultrasound scan type and/or mode.

For example, contrast 431 may include contrast image parameters 441, such as dynamic contrast, Color Rendering Index (CRI) filter, grey map, reject, tint map, monitor setting, Speckle Reduction Imaging (SRI) level, etc. Resolution 432 may include resolution image parameters 442, such as frequency, enhancement, linedensities, SRI level, etc. Brightness 433 may include brightness image parameters 443, such as gain, power, Autobutton, monitor setting, etc. Softness 434 may include softness image parameters 444, such as Linedfilter, Framefilter, CRI level, Enhance, Reject, SRI level, etc. Penetration 435 may include penetration image parameters 445, such as frequency, TGC, power, gain, focus position, as non-limiting examples. Geometry 436, for example, may include geometry image parameters 446, such as depth, zoom, angle, etc. Each of the image parameters 440 that make up the image quality characteristics 430 may be set to certain values in order to form adapted image parameters 440 for each of the image quality characteristics. The image quality characteristics may include values for each of the image parameters that make up the image quality characteristics. In some examples, different image quality characteristics may include the same image parameters, and different image parameters may have the same or different values for image parameters that are included in different image quality characteristics. For example, the image quality parameter of contrast may include a certain value SRI level, and softness may also include a certain value for SRI level. In some examples, the value for SRI level for contrast and the value for SRI level for softness may be the same or different.

Referring to FIG. 1, the signal processor may include a settings processor 150 that comprises suitable logic, circuitry, interfaces, and/or code that may be operable to provide a preset optimization guide and/or settings related to ultrasound image acquisition and/or display, such as image quality characteristics, image parameters, and/or other settings. The preset optimization guide 410 may provide a user interface, configuration tool, menus/sub-menus, and/or other input tools in order to configure/update the image quality settings for obtaining and/or displaying ultrasound images. The preset optimization guide 410 may be an interactive tool to guide the user through configuring, updating, and/or modifying image quality settings of the ultrasound images. In some examples, the preset optimization guide of the settings processor 150 may solicit feedback from the user by presenting the preset optimization guide with a question or series of questions in order to customize image quality characteristics and/or image parameters for the acquisition processor 140 to obtain ultrasound images. The settings processor 150 may ask the user questions related to image quality and/or appearance as described above with regards to FIG. 3.

Additionally and/or alternatively, the settings processor 150 may ask what anatomical structure is being scanned, and/or may load default values and/or preset settings for image quality characteristics and/or image parameters based on the anatomical structure being scanned. The settings processor 150 may then convert or adapt the user answers to the question(s) into image settings such as image quality characteristics and/or image parameters. In some examples, the image quality characteristics and/or image parameters are values. The answers provided by the user may be used in order to determine ultrasound image settings for capturing and/or displaying ultrasound images by the image acquisition processor 140. In some examples, the settings may be provided by the settings processor 150 to the acquisition processor 140, to the adaptation processor 160, and/or may be stored in an archive 138 or other computer readable medium.

Additionally and/or alternatively, the preset optimization guide 410 may provide information regarding the image quality settings, such as the image quality characteristics, image parameters, and/or other ultrasound image settings to educate the user regarding the various settings and how the setting affect the appearance of the ultrasound image. The information may be stored in an archive, or other suitable computer readable medium. In some examples, the information may be presented to the user upon request (e.g., by selection of the setting by the user). In some other examples, the information may be provided within the preset optimization guide and/or provided while the user is inputting feedback for configuration of the settings.

In some examples, once the preset optimization guide has obtained feedback from a user, the settings processor 150 may provide a configuration tool and/or menus/sub-menus to allow a user to update and/or modify image quality characteristics and/or image parameters. The configuration tool 330 may be a knob, a dial, a trackball configuration, and/or another type of user interface that provides functionalities to the user such as reverting back to a previous ultrasound image, toggling between the ultrasound image 330 and an ultrasound image with adapted settings, increasing and/or decreasing settings related to the ultrasound image 330, keeping changes made to the settings, providing a split-screen or side-by-side display depicting both the original ultrasound image and the ultrasound image with updated settings, saving current settings as preset settings, and other functions, as non-limiting examples. Additionally and/or alternatively, the configuration tool 330 of the settings processor 150 may be utilized to configure and/or adjust settings related to the ultrasound image 330, to retrieve settings, and to save the settings in the archive 138 and/or any other suitable data storage medium as preset settings.

In some examples, image quality characteristics may include image parameters with corresponding values. In some examples, each of the image quality characteristics may be increased or decreased by increasing and/or decreasing various image parameters that make up each of the image quality characteristics. For example, when contrast is increased or decreased, values for each of the image parameters may be increased and/or decreased. For example, the image parameters that make up contrast, such as dynamic contrast, Color Rendering Index (CRI) filter, grey map, reject, tint map, monitor setting, Speckle Reduction Imaging (SRI) level, etc. may each be individually increased and/or decreased. In some examples, the values for the image parameters that make up the image quality characteristics may be default settings that are previously configured and/or already saved. In some other examples, the values for the image parameters that make up the image quality characteristics may be input and/or modified by the user and then saved as preset settings.

Figure 4:
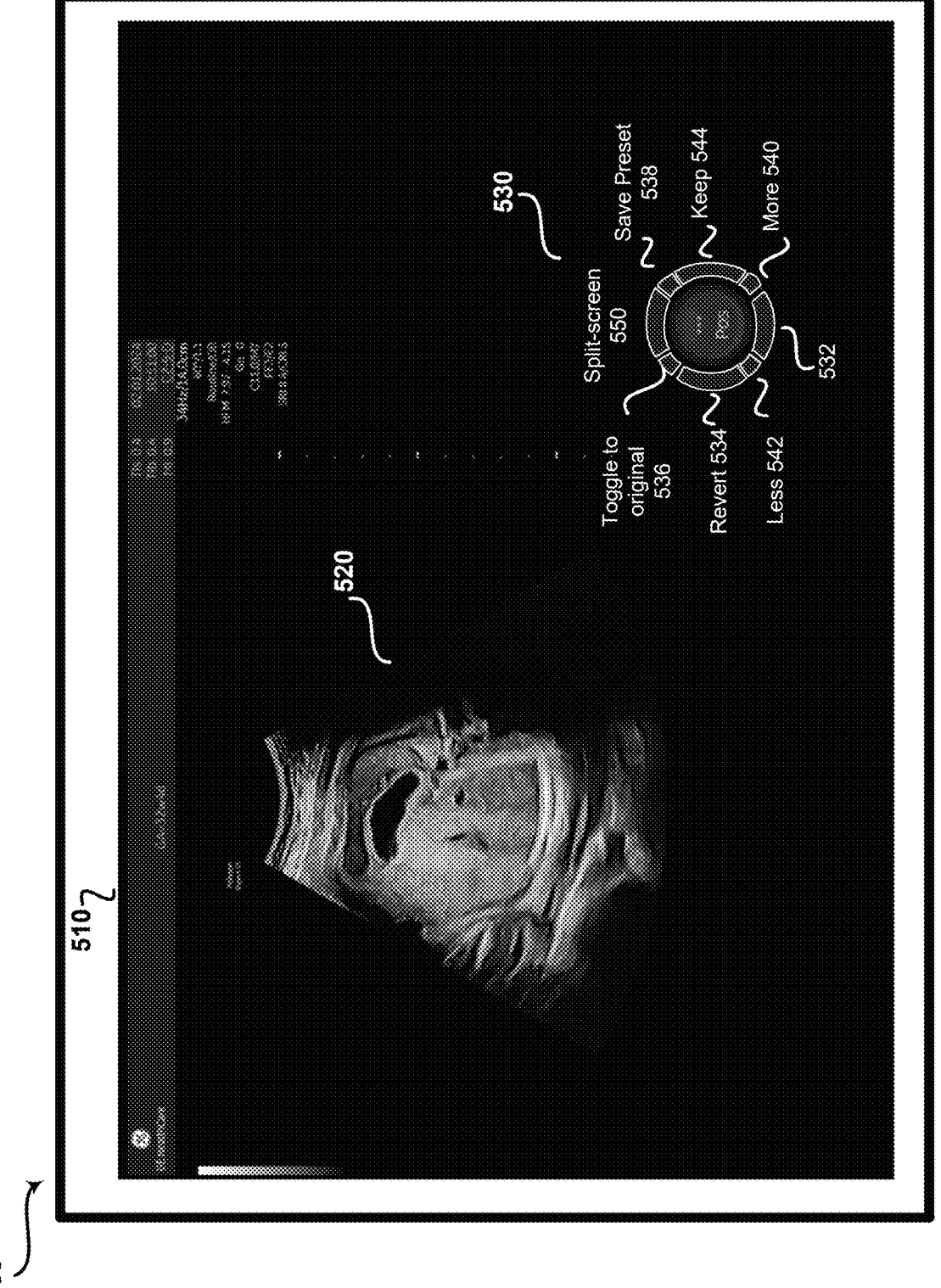
FIG. 4 is an exemplary display of an adapted ultrasound image, in accordance with various embodiments.

FIG. 4 provides a display 500 including a user interface 510, an adapted ultrasound image 520, and a configuration tool 530. The display 500 may include a user interface 510 that includes the ultrasound image 520 and the configuration tool 330. Additionally and/or alternatively, the configuration tool 530 may be a separate user interface on the display 500 and/or may be a separate input device. The user interface 510 may be activated or generated by the acquisition processor 140 and/or the adaptation processor 160. The adapted ultrasound image 520 may be acquired by the ultrasound probe 104 and positioned on the user interface 510 along with the configuration tool 530 by adaptation processor 160.

The configuration tool 530 may be a knob, a dial, and/or a trackball configuration, as non-limiting examples, and/or may include graphical buttons 532 or other icon representing different functionalities in order for a user to provide input for settings related to the adapted ultrasound image 520, as described above. The graphical buttons 532 may represent functionalities such as reverting back to the original ultrasound image 320 of FIG. 2, for example. In some examples, the graphical buttons 532 may be used to toggle between the original ultrasound image 320 of FIG. 2 and the adapted ultrasound image 520, adjusting the appearance of the ultrasound image 520 by increasing or decreasing the image quality characteristics and/or user parameters, keeping changes made to the image appearance, switching to a split-screen or side-by-side display depicting both the original ultrasound image and the adapted ultrasound image, saving current settings as preset settings, as well as other functions, as non-limiting examples.

The configuration tool 530 may be a knob, a dial, a trackball configuration, and/or another type of user interface. In some examples, the configuration tool 530 may include graphical buttons 532 or other icons representing different functionalities in order for a user to provide input for settings related to the ultrasound image 520. For example, the graphical buttons 532 may represent functionalities such as reverting 534 back to a previous ultrasound image, toggling 536 between the ultrasound image 520 and an ultrasound image with adapted settings, increasing and/or decreasing settings (e.g. more 540, less 542) related to the ultrasound image 530, keeping 544 changes made to the settings, providing a split-screen view 550 or side-by-side display depicting both the original ultrasound image and the ultrasound image with updated settings, saving 538 current settings as preset settings, and other functional graphical buttons 532, as non-limiting examples.

Additionally and/or alternatively, the configuration tool 530 may be utilized to configure and/or adjust image quality settings related to the ultrasound image 520, to retrieve image quality settings, and to save the settings in the archive 138 and/or any other suitable data storage medium. In some examples, the stored image quality settings may be stored with a label such as, kidney, cardiac, other anatomical structures, and/or other customized labels so that a user can quickly and efficiently retrieve preset image quality settings, such as image quality characteristics, parameters, and/or other settings that have been modified and saved. In some examples, the ultrasound system 100 may include default settings, image quality characteristics, and/or image parameters which may be updated and/or modified by the configuration tool 530.

Referring to FIG. 1, the signal processor may include an adaptation processor 160 that comprises suitable logic, circuitry, interfaces, and/or code that may be operable to adapt an ultrasound image by modifying image quality characteristics related to ultrasound image appearance. For example, the adaptation processor 160 may receive settings from the settings processor 150, the preset optimization guide, and/or a user interface, and/or may retrieve settings from an archive 138 and/or any other suitable computer readable medium. The adaptation processor 160 may obtain and/or modify the appearance of an ultrasound image obtained by the acquisition processor 140 based on image quality characteristics and/or image parameters input by a user. The adaptation processor 160 may obtain a live view of the ultrasound image for display to the user using the adapted user parameters obtained via user feedback. In some examples, the adaption processor 160 may provide different views of the ultrasound image and the adapted ultrasound image. For example, the adaptation processor 160 may display an ultrasound image, an adapted ultrasound image, both the ultrasound image and the adapted ultrasound image, or may toggle between one or both of the ultrasound images. The image adaptation processor 160 may provide the adapted ultrasound images to a user via display 134 and/or may store the adapted ultrasound images in an archive 138 and/or other computer readable medium.

Figure 5:
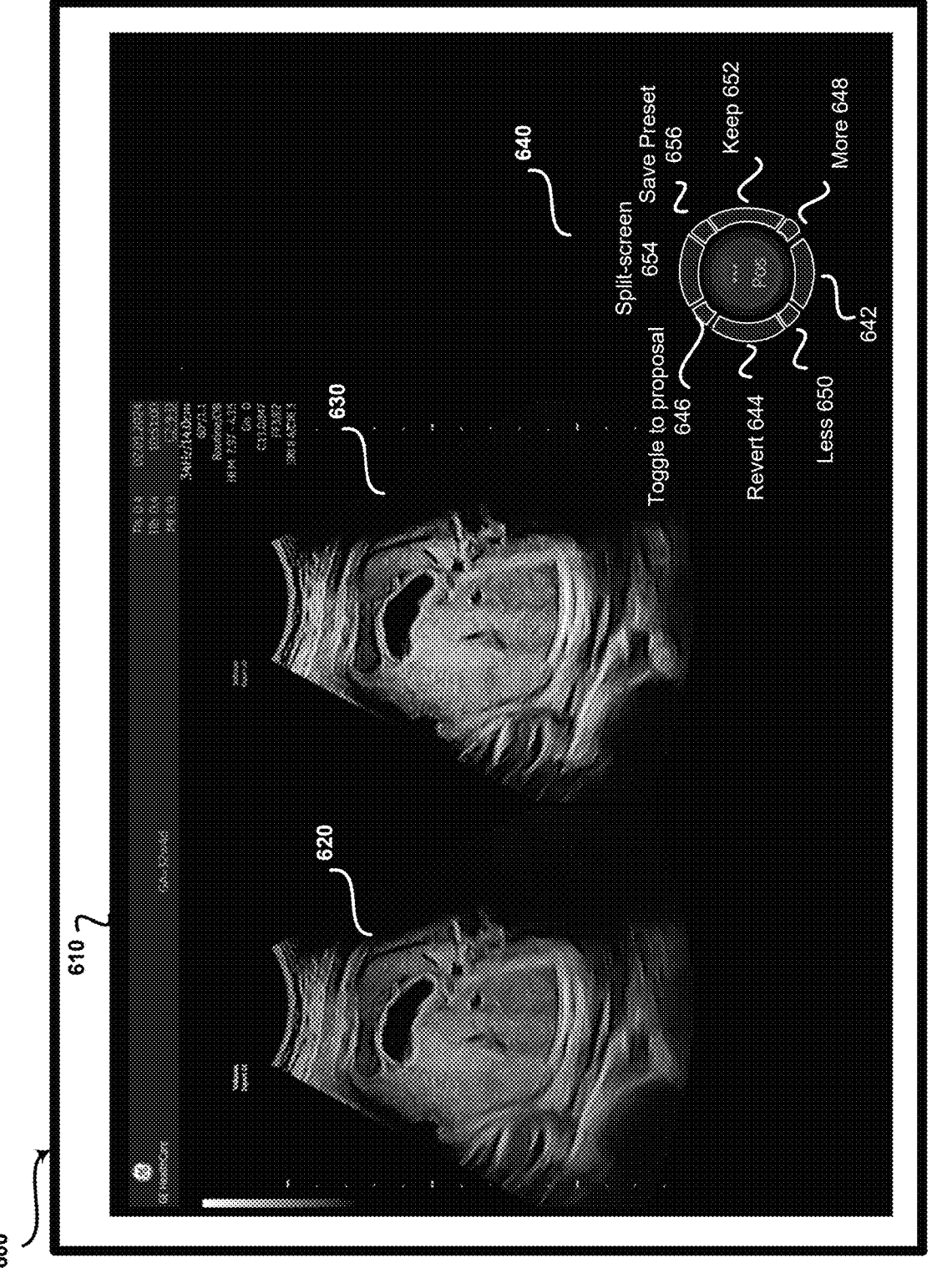
FIG. 5 is an exemplary display including an ultrasound image and an adapted ultrasound image, in accordance with various embodiments.

FIG. 5 provides an exemplary display, a user interface 610, an ultrasound image 620, an adapted ultrasound image 630, and a configuration tool 640, in accordance with various embodiments. In some examples, the user interface 610 includes an ultrasound image 620 and an adapted ultrasound image 630. In some examples, the user interface 610 also includes the configuration tool 640 in order to modify and/or update settings related to image quality/appearance which are reflected in the adapted ultrasound image 630. Although the ultrasound image 620 and the adapted ultrasound image 630 are depicted in a split-screen or side-by-side format, the ultrasound image 620 and the adapted ultrasound image 630 may also be depicted in individually and a user may be allowed to toggle back and forth between the ultrasound image 620 (e.g., ultrasound image 320 in FIG. 2), the adapted ultrasound image 630 (e.g., ultrasound image 520 as depicted in FIG. 4), or the split-screen format with both the ultrasound image 620 and the adapted ultrasound image 630 depicted in FIG. 5. In some examples, the configuration tool 640 may include graphical buttons 642 that allow the user to move between the ultrasound image 620, the adapted ultrasound image 630, and a split-screen or side-by-side display of the ultrasound image 620 and the adapted ultrasound image 630.

The configuration tool 640 may be a knob, a dial, a trackball configuration, and/or another type of user interface 610. In some examples, the configuration tool 640 may include graphical buttons 642 or other icons representing different functionalities in order for a user to provide input for settings related to the ultrasound image 620 and/or ultrasound image 630. For example, the graphical buttons 642 may represent functionalities such as reverting 644 back to a previous ultrasound image, toggling 646 between the original ultrasound image 620 and an adapted ultrasound image 630 with adapted settings, increasing and/or decreasing settings (e.g. more 648, less 650) in ultrasound image 620 and/or adapted ultrasound image 630, keeping 652 changes made to the settings, providing a split-screen view 654 or side-by-side display depicting both the original ultrasound image and the ultrasound image with updated settings, saving 656 current settings as preset settings, and other functional graphical buttons 642 which may be pre-programmed or programmed by a user (e.g. customizable interface functionalities), as non-limiting examples.

In some examples, a preset optimization guide such as described with regards to FIG. 3 may be presented with relation to FIG. 2, 4, or 5. For example, the preset optimization guide may be presented in the same user interface (e.g., user interface 310, 510, 610) and/or display (e.g., display 300, 500, 600) as the ultrasound image (e.g., ultrasound image 320, 620) and/or adapted ultrasound image (e.g., adapted ultrasound image 520, 630), may be overlayed over a portion of the user interface and/or display, may be positioned on the display in combination with ultrasound images, adapted ultrasound images, the configuration tool (e.g., configuration tool 330, 530, 640), etc.

The preset optimization guide may guide the user through questions in order to modify the ultrasound image 620 by updating user parameters (e.g. image parameters 440 of FIG. 3) that make up image quality characteristics (e.g. image quality characteristics 430 of FIG. 3). The user may simultaneously view adapted ultrasound image 630 in order to view, in real-time, the effect that changes in user parameters have on the ultrasound image 620 to produce adapted ultrasound image 630. For example, the preset optimization guide may ask the user whether the user prefers more or less contrast. The user may use the configuration tool 640 to select, More 648 or Less 650. If the user selects More 648, for example, the settings processor 150 may adapt user parameters, such as the adapted image parameters 440 described in FIG. 3.

Based on user input, the settings processor 150 may increase the contrast image quality characteristic by increasing the dynamic contrast parameter (e.g., by incrementing dynamic contrast values by 1 or more), increasing reject parameter (e.g., by increasing the grey map values by 10 or more), and/or increasing CRI filter (e.g., by incrementing a level, such as from low to mid-level, mid-level to high-level, etc.), and/or by increasing/decreasing other user parameters that may be used to modify the image quality characteristic. In response to the increase in contrast, the adaptation processor 160 may update the adapted ultrasound image 630. If, for example, the user would like to further adjust the image, the user may select More 648 a second time, in which case, the settings processor 150 may again increase the values of the dynamic contrast, grey map, and CRI filter parameters, which may be reflected in the adapted ultrasound image 630. The user may continue to increase the contrast by selecting More 648, or the user may also decrease the contrast (e.g., Less 650), which is reflected by changes in appearance to the adapted ultrasound image 630 on the display 600. If, for example, the contrast is increased to an unacceptable level in the ultrasound image 630 as viewed on the user interface 610, the user may select Less 650 to decrease the contrast by decreasing the image parameters related to contrast. Once the adapted ultrasound image 630 is acceptable to the user, the user may select Keep 652 in order to select the settings for displaying the ultrasound image 630. Additionally and/or alternatively, the user may select Save Preset 656 in order to save the selected parameters as preset settings. Saving the selected image quality parameters may overwrite current preset settings or a user may be prompted to save as new settings, default settings, etc. In some examples, once the user keeps and/or saves the preset, the preset optimization guide may provide a notification that the settings have been configured and/or updated and may exit the preset optimization guide.

In another example, the preset optimization guide may ask a user whether the user prefers more or less brightness. The user may select More 648 or Less 650 as described. Additionally and/or alternatively, the user may select Keep 652, which indicates the brightness is at an acceptable level. The preset optimization guide may then proceed to the next question and may ask, for example, whether the user prefers a higher axial resolution. The user may then select More 648, Less 650, and/or Keep 652 as described above. If a user selects More 648, for example, in order to increase the axial resolution, the settings processor 150 may increase the frequency parameter (e.g. by increasing from harmonic mid-level to high-level), increase the enhance parameter (e.g. by increasing a level, such as level 2 to level 3), and/or increase or decrease other parameters that make up the axial resolution image quality characteristic, which simultaneously updates the adapted ultrasound image 630 in the display 600. Once the user reaches an acceptable level for the axial resolution, the user may select Keep 652 in order to retain the values for the axial resolution image quality characteristic. The preset optimization user guide may proceed to ask whether the user would prefer a higher lateral resolution. In some examples, when the user selects More 648, the settings processor 150 may increase a line density parameter (e.g., from mid-level to high-level), and/or increase or decrease other parameters related to the resolution image quality characteristic. In some examples, the adapted ultrasound image 630 is simultaneously updated while the ultrasound image 620 remains on the user interface 610 so that the user may compare the appearance of the ultrasound images.

The preset optimization guide may continue asking questions for additional image quality characteristics until all questions for different image quality characteristics have been asked and/or until the user selects Save Preset 656. Saving the selected image quality parameters may overwrite current preset settings or a user may be prompted to save as new settings, default settings, etc. In some examples, once the user keeps and/or saves the preset, the preset optimization guide may provide a notification that the settings have been configured and/or updated and may exit the preset optimization guide.

Figure 6:
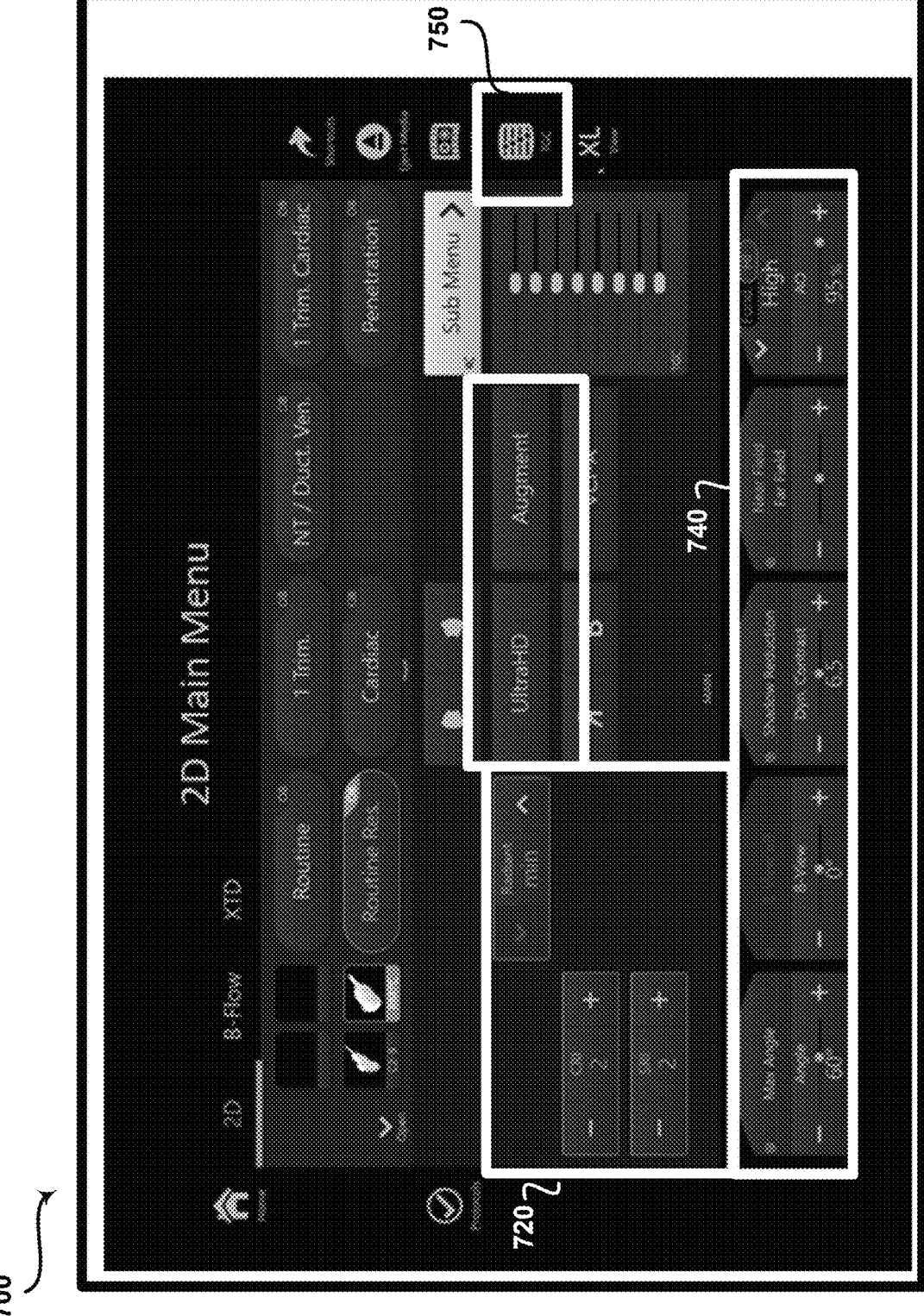
FIG. 6 is an exemplary display including an exemplary menu of a preset optimization quick guide, in accordance with various embodiments.

FIG. 6 is an exemplary display 700 including an exemplary user interface 710 for providing a main menu to modify settings related to image quality/appearance, in accordance with various embodiments. The display 700 includes a user interface 710 that includes image quality characteristics and/or image parameters that may be individually modified by a user. The user interface, image quality characteristics, and image parameters presented may be based on the ultrasound mode being used. For example, the user interface 710 may be a 2D user interface 710 that includes settings for manually updating image parameters such as Radiant, CRI, SRI, etc. In some examples, the user interface 710 may be a Main Menu for settings related to a 2D ultrasound image that includes image parameters 720 730 740 750 that may be adjusted by the user. In some examples, the image parameters 720 730 may be CRI, SRI, Radiant, UltraHD, Augment, etc. Additionally and/or alternatively, the user interface 710 may include image parameters 740 such as Angle, B-View, Shadow Reduction, Near Field and/or Far Field, AO, and/or settings 750 such as Time Gain Compensation (TGC). The image parameters 730 740 750 may be placed in different portions of the user interface 710 or may be placed in a separate user interface. In some examples, the selection of an image parameter 720 730 740 750 from the 2D Main Menu may generate a Sub-Menu, such as the sub-menu described below with regard to FIG. 7.

Figure 7:
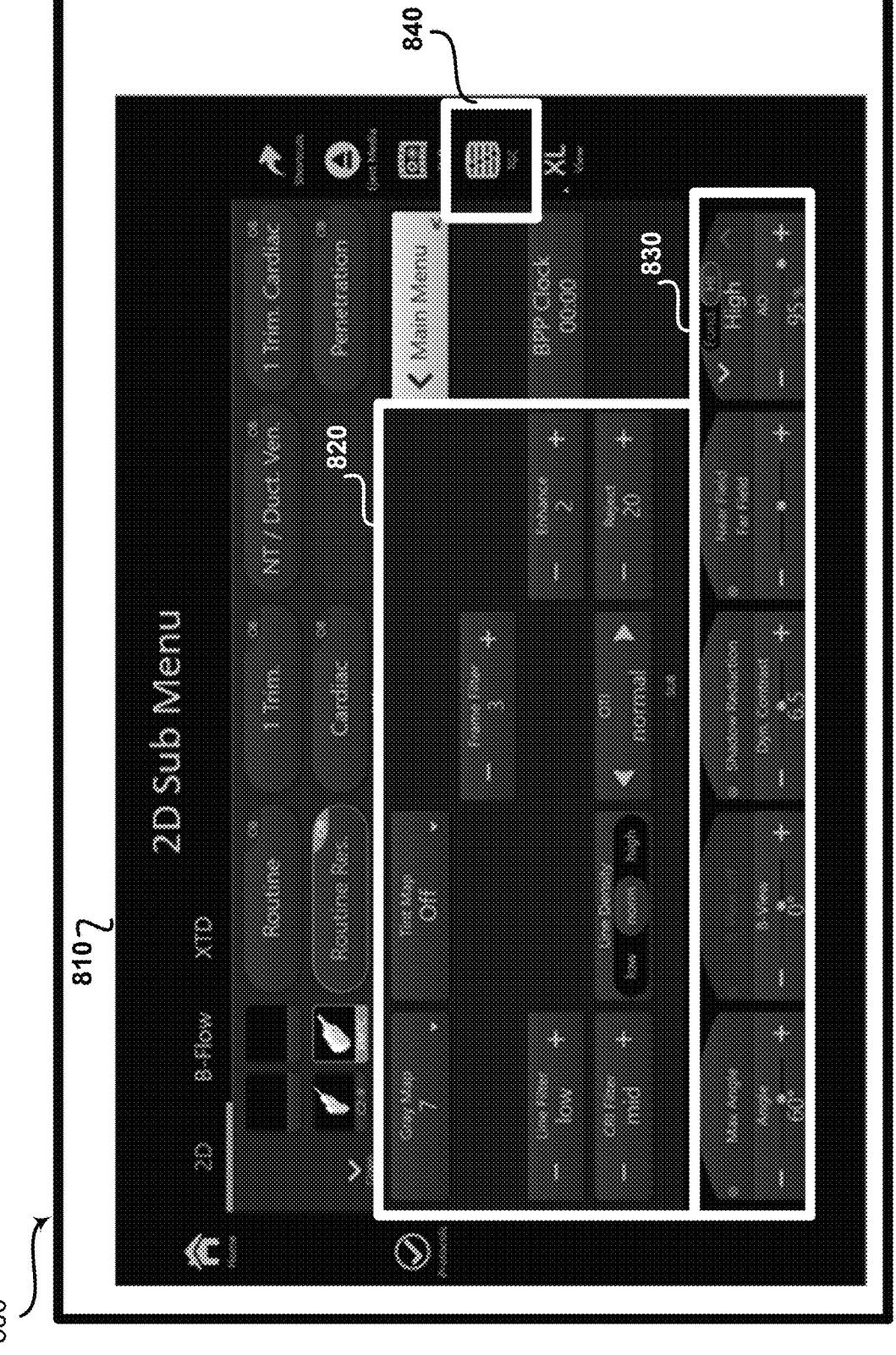
FIG. 7 is an exemplary display including an exemplary sub-menu of a preset optimization quick guide, in accordance with various embodiments.

FIG. 7 is an exemplary display 800 including an exemplary user interface 810 for a sub-menu for modifying settings related to image quality/appearance, in accordance with various embodiments. The display 800 includes a user interface 810 that includes image quality characteristics and/or image parameters that may be individually modified by a user. The user interface 810 may include settings for manually updating image parameters for a 2D ultrasound, such as Gray Map, Tint Map, Frame Filter, Line Filter, CRI Filter, Line Density, Enhance, OTI, Reject, as non-limiting examples. Additionally and/or alternatively, the user interface 810 may include image parameters 830 that may be adjusted, such as Angle, β-View, Shadow Reduction, Near Field and/or Far Field, AO, and/or settings 840 such as Time Gain Compensation (TGC). The image parameters, image quality characteristics, and/or user interface 910 presented may be based on the ultrasound mode being used. The image parameters 820 830 840 may be placed in different portions of the user interface 810 or may be placed in a separate user interface.

Figure 8:
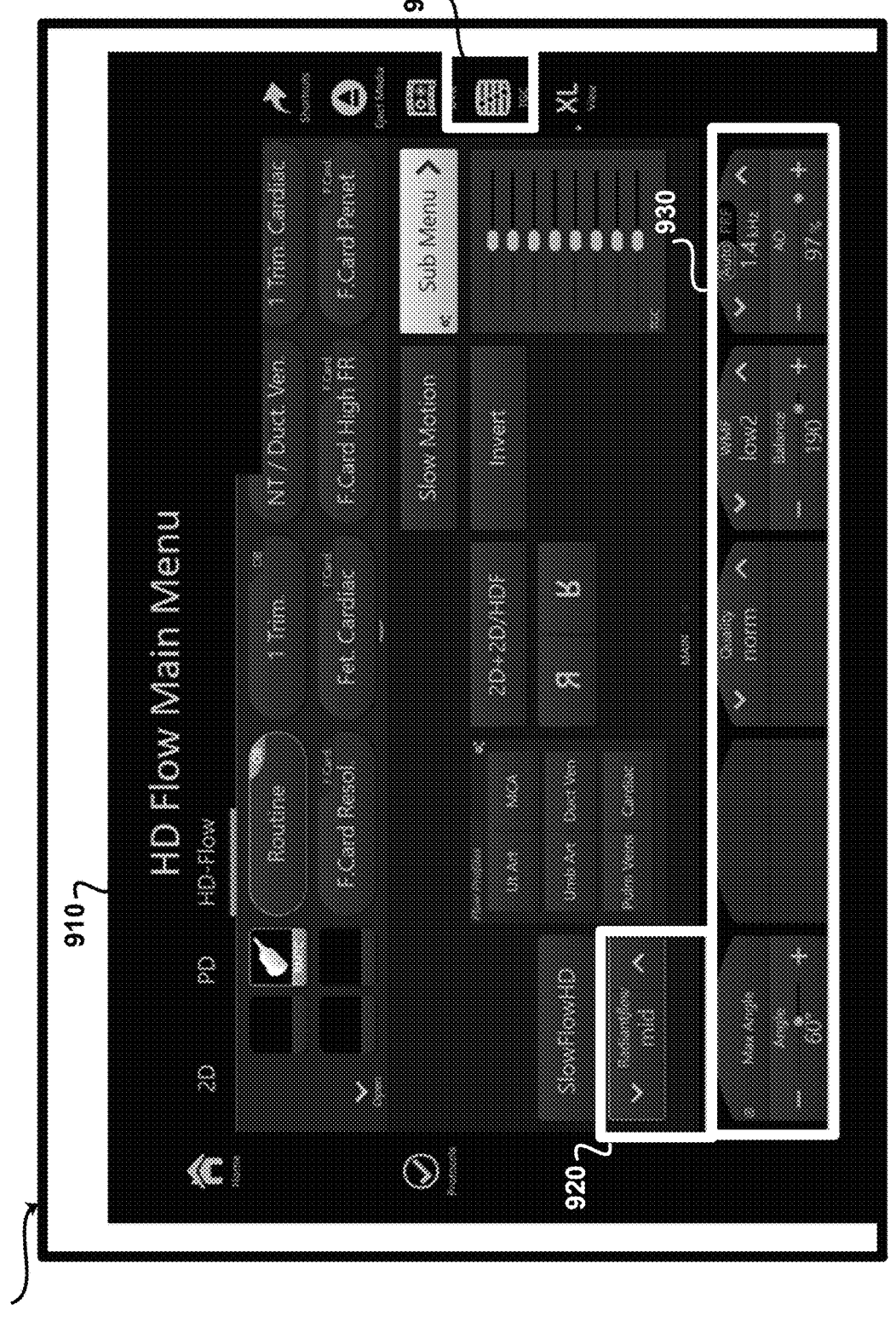
FIG. 8 is an exemplary display including a second exemplary menu of a preset optimization quick guide, in accordance with various embodiments.

FIG. 8 is an exemplary display 900 including a second exemplary user interface 910 for a main menu for modifying settings related to image quality/appearance, in accordance with various embodiments. The display 900 includes a user interface 910 that includes image quality characteristics and/or image parameters that may be individually modified by a user. The user interface may include settings for manually updating image parameters such as Radiant, CRI, SRI, etc. The image parameters, image quality characteristics, and/or user interface 910 presented may be based on the ultrasound mode being used. In some examples, the user interface 910 may be an HD Sub-Menu that includes image parameters 920 930 940 that may be adjusted by the user. In some examples, the user may select image parameters such as CRI, SRI, or Radiant. Additionally and/or alternatively, the user may select image parameters 920 such as Radiant-flow, settings 930 such as Angle, Quality, WMF, Auto/PRF, and/or settings 940 such as TGC. In some examples, the selection of a setting 920 930 940 from the HD Main Menu may generate a Sub-Menu, such as the sub-menu described below with regard to FIG. 9.

Figure 9:
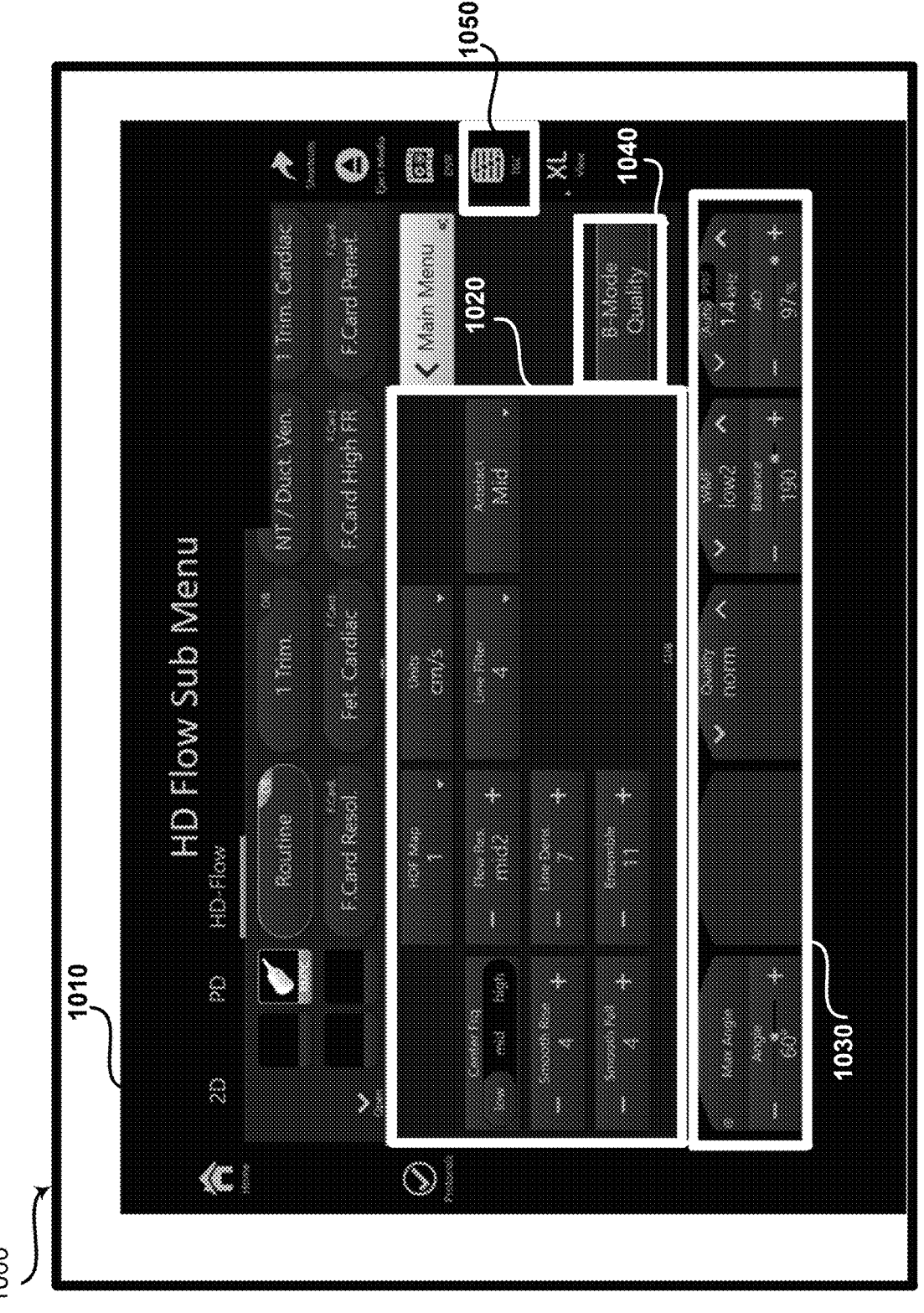
FIG. 9 is an exemplary display including a second exemplary sub-menu of a preset optimization quick guide, in accordance with various embodiments.

FIG. 9 is an exemplary display 1000 including a second exemplary user interface 1010 for a sub-menu for modifying settings related to image quality/appearance, in accordance with various embodiments. In some examples, the user interface 1010 is a High Definition (HD) sub-menu. The user interface 1010 may include image parameters 1020 1030 1040 1050 for manually modifying and/or configuring image quality characteristics and/or characteristics for an HD ultrasound such as HDF Map, Units, Center Frequency, Flow Resolution, Line Filter Artefact, Smooth Rise, Line Density, Smooth Fall, Ensemble, as non-limiting examples. Additionally and/or alternatively, the user interface 1010 may include image parameters 1030 1040 1050 that may be adjusted and/or configured, such as Max Angle, Quality, WMF, Auto/PRF, B-Mode Quality, Time Gain Compensation (TGC), or other parameters, as non-limiting examples. The image parameters, image quality characteristics, and/or user interface 910 presented may be based on the ultrasound mode being used. The image parameters 1020 1030 1040 may be placed in different areas of the user interface 1010 or may be placed in a separate user interface.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present ultrasound images 320 520 620 630, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

In various embodiments, the archive 138 stores ultrasound images 320 520 620 630, instructions for acquiring ultrasound images 320 520 620 630, instructions for activating a user interface, instructions for presenting one or more image quality characteristics for acquiring ultrasound images, instructions for receiving feedback for adjusting image quality characteristics, instructions for adapting the ultrasound images based on the feedback, instructions for reverting to the ultrasound images, instructions for obtaining the adapted ultrasound images, instructions for further adjusting image quality characteristics or additional image quality characteristics, and instructions for obtaining the adapted ultrasound images.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the image acquisition processor 140, the settings processor 150, and/or the adaptation processor 160. For example, the artificial intelligence model inferenced by the settings processor 150 and/or the adaptation processor 160 may be trained to automatically identify adapted user parameters from ultrasound images using database(s) 220 of classified ultrasound images of anatomical structures. As another example, the artificial intelligence model inferenced by the settings processor 150 and/or adaptation processor 160 may be trained to automatically identify image quality characteristics, image parameters, and the like in an ultrasound image using database(s) 220 of classified ultrasound images and/or motion parameters.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms. In some examples, the training image databases 220 may be integrated with the archive 138 or vice versa.

Figure 10:
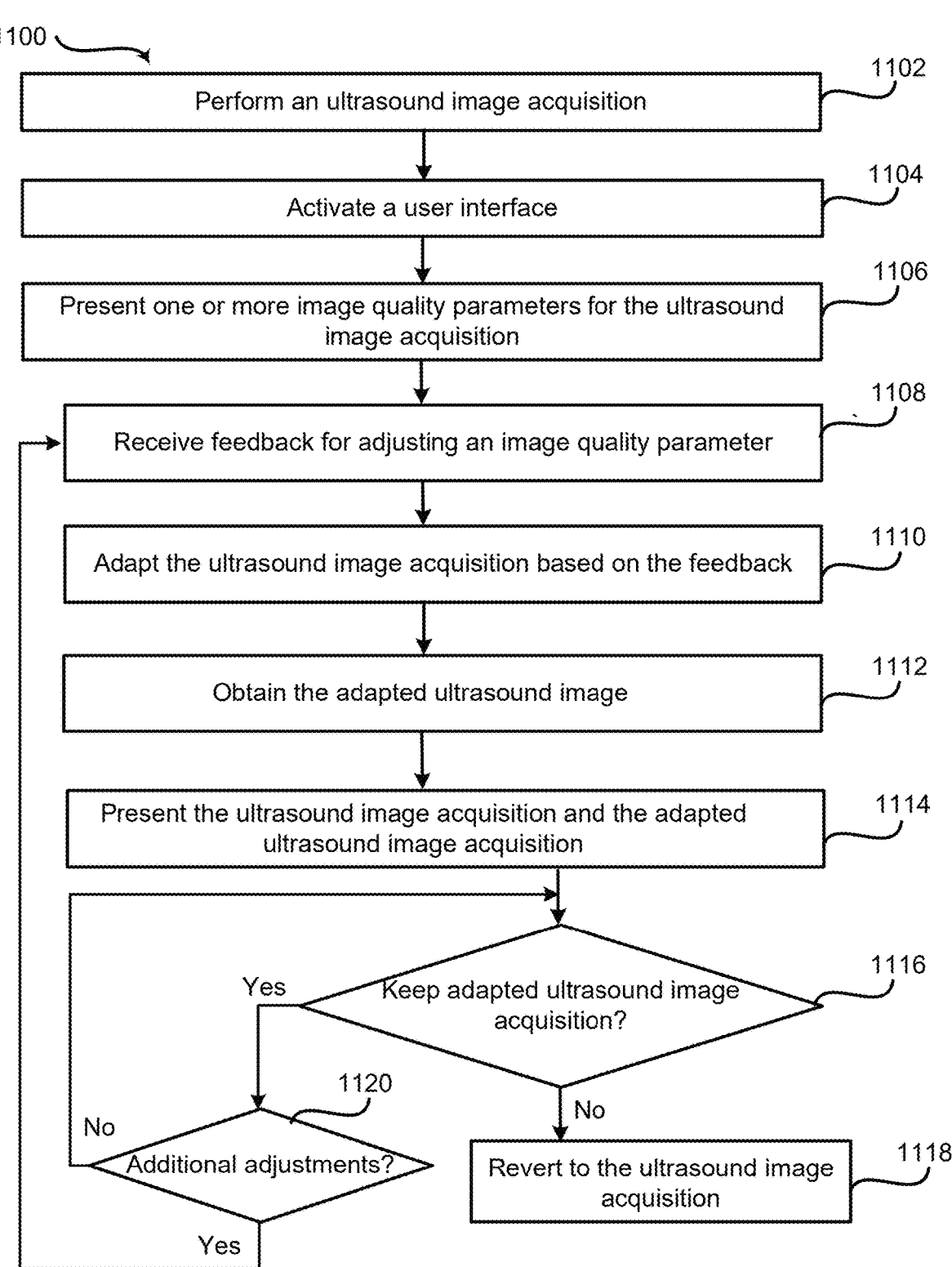
FIG. 10 is a flow chart illustrating exemplary steps 1102-1118 that may be utilized for adapting ultrasound images using a preset optimization quick guide, in accordance with various embodiments.

FIG. 10 is a flow chart 1100 illustrating exemplary steps 1102-1120 that may be utilized for adapting ultrasound images using a preset optimization quick guide, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 1102, a signal processor 132, 140 of the ultrasound system 100 may be configured to acquire ultrasound images 320, 520, 620, 630. For example, an image acquisition processor 140 may be configured to acquire ultrasound images 320, 520, 620, 630 using an ultrasound probe 104. The acquired ultrasound images 320, 520, 620, 630 may be displayed and/or stored at archive 138 and/or any suitable computer readable medium.

At step 1104, a signal processor 132, 140 of the ultrasound system 100 may be configured to activate a user interface to display the acquired ultrasound images 320, 520, 620, 630. For example, the image acquisition processor 140 may be configured to activate the user interface to display the ultrasound images 320, 520, 620, 630, which may be stored by the acquisition processor 140 in an archive 138 or other suitable computer readable medium.

At step 1106, a signal processor 132, 150 of the ultrasound system 100 may be configured to present one or more image quality characteristics for the acquisition of the ultrasound images 320, 520, 620, 630 by the image acquisition processor 140. For example, the settings processor 150 may be configured to provide a preset optimization guide 410 as a user interface that allows a user to input, update, and/or modify image quality characteristics, image parameters, and/or other settings. In some examples, the settings processor 150 may store the preset optimization guide in an archive 138 or other suitable computer readable medium, and/or provided to the adaptation processor 160.

At step 1108, signal processor 132, 150 of the ultrasound system 100 may be configured to receive feedback for adjusting image quality characteristics. For example, a settings processor 150 may be configured to solicit feedback from the user by presenting a preset optimization guide with a question or series of questions in order to customize image quality characteristics and/or image parameters for the acquisition processor 140 to obtain ultrasound images. Additionally and/or alternatively, the settings processor 150 may ask what anatomical structure is being scanned, and/or may load default values and/or preset settings for image quality characteristics and/or image parameters based on the anatomical structure being scanned. The settings processor 150 may then convert or adapt the user answers to the question(s) into image settings such as image quality characteristics and/or image parameters. The image settings may be stored by the settings processor 150 and/or provided to the adaptation processor 160.

At step 1110, a signal processor 132, 160 of the ultrasound system 100 may be configured to adapt the ultrasound image acquisition by the ultrasound probe 104 based on the feedback. For example, the adaptation processor 160 may provide the adapted user parameters to the acquisition processor 140 and/or store the adapted user parameters in an archive and/or a suitable computer readable storage medium.

At step 1112, a signal processor 132, 160 of the ultrasound system 100 may be configured to obtain the adapted ultrasound image acquisition using the adapted user parameters. For example, the adaptation processor 160 may use the adapted user parameters in order to obtain adapted ultrasound images or the user may adapt an ultrasound image that has already been obtained.

At step 1114, a signal processor 132, 160 of the ultrasound system 100 may be configured to present the ultrasound image and the adapted ultrasound image. For example, the adaptation processor 160 may present the ultrasound image and the adapted ultrasound image for comparison. In some examples, the adaptation processor 160 may present the ultrasound image and the adapted ultrasound image simultaneously in a split-screen format, individually so that a user may toggle back and forth between the ultrasound image, the adapted ultrasound image 630, or the split-screen format with both the ultrasound image 620 and the adapted ultrasound image 630.

At step 1116, a signal processor 132, 160 of the ultrasound system 100 may be configured to present the ultrasound image and the adapted ultrasound image so that a user may select whether to keep the adapted ultrasound image obtained with the adapted user parameters. For example, the adaptation processor 160 may be configured to provide a user interface such as a configuration tool to receive input from a user to keep the adapted image settings.

At step 1118, a signal processor 132, 160 of the ultrasound system 100 may be configured to present the ultrasound image and the adapted ultrasound image so that a user may select to revert the adapted ultrasound image obtained with the adapted user parameters to the ultrasound image without the adapted user parameters. For example, the adaptation processor 160 may be configured to provide a user interface such as a preset optimization guide, a configuration tool, a menu, and/or sub-menus to receive input from a user to revert the adapted image settings.

At step 1120, a signal processor 132, 160 of the ultrasound system 100 may be configured to present the ultrasound image and the adapted ultrasound image so that a user may select to further adjust an image quality parameter or an additional image quality characteristic. For example, the adaptation processor 160 may be configured to provide a user interface 310, 510, 610, 710, 810 such as a preset optimization guide, a configuration tool, a menu, and/or sub-menus to receive input from a user to further adjust an image quality parameter or an additional image quality characteristic. If the user selects to further adjust an image quality parameter or an additional image quality characteristic, the method 1100 returns to step 1108.

Aspects of the present disclosure provide a method 1100 and system 100 for improved image quality in ultrasound scans including performing an ultrasound image acquisition 320, 620, using an ultrasound probe 104. The method 1100 includes activating, by at least one processor 132, 140, a user interface 310, 510, 610, 710, 810 and presenting, by the at least one processor 132, 140, via the user interface 310, 510, 610, 710, 810, one or more image quality characteristics 430 for the ultrasound image acquisition 320, 620.

The method 1100 further includes receiving feedback, by the at least one processor 132, 150, for adjusting an image quality characteristic 430 of the one or more image quality characteristics 430, wherein the image quality parameter 430 comprises adapted image parameters 440. The method 1100 includes adapting, by the at least one processor 132, 160, the ultrasound image acquisition 320, 620, based on the feedback, to adjust the image quality characteristic 430 and produce an adapted ultrasound image acquisition 520, 630 by modifying the one or more adapted image parameters 440, and presenting, by the at least one processor 132, 140, 160, the ultrasound image acquisition 320, 620 and the adapted ultrasound image acquisition 520, 630 via the user interface 310, 510, 610, 710, 810.

In an exemplary embodiment, the includes, based on a user selection, performing one of: reverting, by the at least one processor 132, 150, to the ultrasound image acquisition 320, 620, obtaining the adapted ultrasound image acquisition 520, 630 with the ultrasound probe 104 using the modified one or more image parameters 140 of the adapted ultrasound image acquisition 520, 630, and further adjusting the one or more image quality characteristics 430 or an additional image quality characteristic of the one or more image quality characteristics 430.

In an exemplary embodiment, the method 1100 further includes modifying an additional image quality characteristic of the one or more image quality characteristics 430 on the ultrasound image acquisition 320, 620 or the adapted ultrasound image acquisition 520, 630 based on additional user input.

In an exemplary embodiment, the method 1100 further includes saving the modified one or more adapted image parameters 440 as a preset setting. In an exemplary embodiment, the presenting, by the at least one processor 132, 140, the ultrasound image acquisition 320, 620 and the adapted ultrasound image acquisition 520, 630 via the user interface 310, 510, 610, 710, 810 includes simultaneously displaying the ultrasound image acquisition 320, 620 and the adapted ultrasound image acquisition 520, 630 in a side-by-side display on the user interface 310, 510, 610, 710, 810.

In an exemplary embodiment, the user interface 310, 510, 610, 710, 810 is an interactive tool that presents the one or more image quality characteristics 430 via a series of questions. In an exemplary embodiment, the series of questions are based on a type of ultrasound scan or an anatomical structure being scanned.

In an exemplary embodiment, the ultrasound image acquisition 320, 620 and the adapted ultrasound image acquisition 520, 630 via the user interface 310, 510, 610, 710, 810 include displaying the ultrasound image acquisition 320, 620 and the adapted ultrasound image acquisition 520, 630 in a toggling display on the user interface 310, 510, 610, 710, 810.

In an exemplary embodiment, the user interface 310, 510, 610, 710, 810 is an interactive tool that provides information regarding the one or more image quality characteristics 430 while presenting the one or more image quality characteristics 430.

Various embodiments provide an ultrasound system 100 for improved image quality in ultrasound scans including an ultrasound probe 104 configured to perform an ultrasound image acquisition 320, 620 and at least one processor 132, 140 configured to activate a user interface 310, 510, 610, 710, 810, present, via the user interface 310, 510, 610, 710, 810, one or more image quality characteristics 430 for the ultrasound image acquisition 320, 620, receive feedback for adjusting an image quality characteristic of the one or more image quality characteristics 430, wherein the image quality characteristic comprises one or more image quality parameters 440, adapt the ultrasound image acquisition 320, 620 based on the feedback, to adjust the image quality characteristic 430 and produce an adapted ultrasound image acquisition 520, 630 by modifying the one or more adapted image quality parameters 440, present the ultrasound image acquisition 320, 620 and the adapted ultrasound image acquisition 520, 630 via the user interface 310, 510, 610, 710, 810, and, based on a user selection: revert to the ultrasound image acquisition 320, 620, obtain the adapted ultrasound image acquisition 520, 630 using the modified one or more adapted image quality parameters 440 of the adapted ultrasound image acquisition 520, 630, or further adjust the image quality parameter or an additional image quality characteristic of the one or more image quality characteristics 430.

In a representative embodiment, the at least one processor 132, 150 is further configured to modify the additional image quality characteristic of the one or more image quality characteristics 430 on the ultrasound image acquisition 320, 620 or the adapted ultrasound image acquisition 520, 630 based on additional user input.

In a representative embodiment, the at least one processor 132, 150 is further configured to save the modified one or more adapted image quality parameters 440 as a preset setting. In a representative embodiment, the at least one processor 132, 140, 160 is configured to present the ultrasound image acquisition 320, 620 and the adapted ultrasound image acquisition 520, 630 via the user interface 310, 510, 610, 710, 810 by displaying the ultrasound image acquisition 320, 620 and the adapted ultrasound image acquisition 520, 630 in a side-by-side display or toggling display on the user interface 310, 510, 610, 710, 810.

In a representative embodiment, the user interface 310, 510, 610, 710, 810 is an interactive tool that presents the one or more image quality characteristics 430 via a series of questions. In a representative embodiment, the series of questions are based on a type of ultrasound scan or an anatomical structure being scanned.

In a representative embodiment, the user interface 310, 510, 610, 710, 810 is an interactive tool that provides information regarding the one or more image quality characteristics 430 while presenting the one or more image quality characteristics 430.

Various embodiments provide an ultrasound system 100 for improved image quality in ultrasound imaging comprising: an ultrasound probe configured to performing an ultrasound image acquisition 320, 620 and at least one processor 132, 140, 150, 160 configured to: activate a user interface 310, 510, 610, 710, 810, present, via the user interface 310, 510, 610, 710, 810, one or more image quality characteristics 430 of the ultrasound image acquisition, receive feedback regarding an image quality characteristic of the one or more image quality characteristics 430, wherein the image quality parameter comprises adapted image quality parameters 440, modify the image quality parameters 440 based on the feedback to adjust the image quality characteristic and produce an adapted ultrasound image acquisition 520, 630, present the ultrasound image acquisition 320, 620 and the adapted ultrasound image acquisition 520, 630 via the user interface 310, 510, 610, 710, 810, present options to revert to the ultrasound image acquisition 320, 620, retain the adapted ultrasound image acquisition 520, 630, or adjust the adapted ultrasound image acquisition 520, 630 by further adjusting the image quality characteristic or an additional image quality characteristic of the one or more image quality characteristics 430, and based on a user selection of the options, revert to the ultrasound image acquisition 320, 620, retain the adapted ultrasound image acquisition 520, 630, or present the one or more image quality characteristics 430 via the user interface 310, 510, 610, 710, 810.

In a representative embodiment, the at least one processor 132, 150 is further configured to modify the additional image quality characteristic of the one or more image quality characteristics 430 on the ultrasound image acquisition 320, 620 or the adapted ultrasound image acquisition 520, 630 based on additional user input.

In a representative embodiment, the at least one processor 132, 150 is further configured to save the modified characteristics as a preset setting. In a representative embodiment, the at least one processor 132, 140, 160 is configured to present the ultrasound image acquisition 320, 620 and the adapted ultrasound image acquisition 520, 630 via the user interface 310, 510, 610, 710, 810 by displaying the ultrasound image acquisition 320, 620 and the adapted ultrasound image acquisition 520, 630 in a side-by-side display or toggling display on the user interface 310, 510, 610, 710, 810.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As a non-limiting example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for acquiring a target ultrasound image having a target view of one or more anatomical structures.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for improved image quality in ultrasound scans comprising:
   performing an ultrasound image acquisition using an ultrasound probe;
   activating, by at least one processor, a user interface;
   presenting, by the at least one processor, via the user interface, a plurality of image quality characteristics for the ultrasound image acquisition;
   receiving feedback, by the at least one processor, for adjusting an image quality characteristic of the plurality of image quality characteristics, wherein each of the plurality of image quality characteristics comprises a plurality of image quality parameters;
   adapting, by the at least one processor, the ultrasound image acquisition based on the feedback, to adjust the image quality characteristic and produce an adapted ultrasound image acquisition by modifying the plurality of image quality parameters; and presenting, by the at least one processor, the ultrasound image acquisition and the adapted ultrasound image acquisition via the user interface.

2. The method of claim 1, further comprising, based on a user selection, performing one of:
   reverting, by the at least one processor, to the ultrasound image acquisition;
   obtaining the adapted ultrasound image acquisition with the ultrasound probe using the modified plurality of image quality parameters of the adapted ultrasound image acquisition; and
   further adjusting the image quality characteristic or an additional image quality characteristic of the plurality of image quality characteristics.

3. The method of claim 1, further comprising modifying an additional image quality characteristic of the plurality of image quality characteristics on the ultrasound image acquisition or the adapted ultrasound image acquisition based on additional user input.

4. The method of claim 1, further comprising saving the modified plurality of image quality parameters as a preset setting.

5. The method of claim 1, wherein presenting, by the at least one processor, the ultrasound image acquisition and the adapted ultrasound image acquisition via the user interface comprises simultaneously displaying the ultrasound image acquisition and the adapted ultrasound image acquisition in a side-by-side display on the user interface.

6. The method of claim 1, wherein the user interface is an interactive tool that presents the plurality of image quality characteristics via a series of questions.

7. The method of claim 6, wherein the series of questions are based on a type of ultrasound scan or an anatomical structure being scanned.

8. The method of claim 1, wherein presenting, by the at least one processor, the ultrasound image acquisition and the adapted ultrasound image acquisition via the user interface comprises displaying the ultrasound image acquisition and the adapted ultrasound image acquisition in a toggling display on the user interface.

9. The method of claim 1, wherein the user interface is an interactive tool that provides information regarding the plurality of image quality characteristics or the plurality of image quality parameters while presenting the plurality of image quality characteristics or the plurality of image quality parameters.

10. An ultrasound system for improved image quality in ultrasound scans comprising:
   an ultrasound probe configured to perform an ultrasound image acquisition;
   at least one processor configured to:
      activate a user interface;
      present, via the user interface, a plurality of image quality characteristics for the ultrasound image acquisition;
      receive feedback for adjusting an image quality characteristic of the plurality of image quality characteristics, wherein each of the plurality of image quality characteristic comprises a plurality of image quality parameters;
      adapt the ultrasound image acquisition based on the feedback, to adjust the image quality characteristic and produce an adapted ultrasound image acquisition by modifying the plurality of image quality parameters;

present the ultrasound image acquisition and the adapted ultrasound image acquisition via the user interface; and based on a user selection:

revert to the ultrasound image acquisition, obtain the adapted ultrasound image acquisition using the modified plurality of image quality parameters of the adapted ultrasound image acquisition, or further adjust the image quality characteristic or an additional image quality characteristic of the plurality of image quality characteristics.

11. The ultrasound system of claim 10, wherein the at least one processor is further configured to modify the additional image quality characteristic of the plurality of image quality characteristics on the ultrasound image acquisition or the adapted ultrasound image acquisition based on additional user input.

12. The ultrasound system of claim 10, wherein the at least one processor is further configured to save the modified plurality of image quality parameters as a preset setting.

13. The ultrasound system of claim 10, wherein the at least one processor is configured to present the ultrasound image acquisition and the adapted ultrasound image acquisition via the user interface by displaying the ultrasound image acquisition and the adapted ultrasound image acquisition in a side-by-side display or toggling display on the user interface.

14. The ultrasound system of claim 10, wherein the user interface is an interactive tool that presents the plurality of image quality characteristics via a series of questions.

15. The ultrasound system of claim 14, wherein the series of questions are based on a type of ultrasound scan or an anatomical structure being scanned.

16. The ultrasound system of claim 10, wherein the user interface is an interactive tool that provides information regarding the plurality of image quality characteristics or the plurality of image quality parameters while presenting the plurality of image quality characteristics or the plurality of image quality parameters.

17. An ultrasound system for improved image quality in ultrasound imaging comprising:

an ultrasound probe configured to perform an ultrasound image acquisition;

at least one processor configured to:

activate a user interface;

present, via the user interface, a plurality of image quality characteristics of the ultrasound image acquisition;

receive feedback regarding an image quality characteristic of the plurality of image quality characteristics, wherein each of the plurality of image quality characteristic comprises a plurality of image quality parameters;

modify the plurality of image quality parameters based on the feedback to adjust the image quality characteristic and produce an adapted ultrasound image acquisition;

present the ultrasound image acquisition and the adapted ultrasound image acquisition via the user interface;

present options to revert to the ultrasound image acquisition, retain the adapted ultrasound image acquisition, or adjust the adapted ultrasound image acquisition by further adjusting the image quality characteristic or an additional image quality characteristic of the plurality of image quality characteristics; and based on a user selection of the options, revert to the ultrasound image acquisition, retain the adapted ultrasound image acquisition, or present the plurality of image quality characteristics via the user interface.

18. The ultrasound system of claim 17, wherein the at least one processor is further configured to modify the additional image quality characteristic of the plurality of image quality characteristics on the ultrasound image acquisition or the adapted ultrasound image acquisition based on additional user input.

19. The ultrasound system of claim 17, wherein the at least one processor is further configured to save the modified image quality parameters as a preset setting.

20. The ultrasound system of claim 17, wherein the at least one processor is configured to present the ultrasound image acquisition and the adapted ultrasound image acquisition via the user interface by displaying the ultrasound image acquisition and the adapted ultrasound image acquisition in a side-by-side display or toggling display on the user interface.

21. The ultrasound system of claim 17, wherein the user interface is an interactive tool that presents the plurality of image quality characteristics via a series of questions.

22. The ultrasound system of claim 21, wherein the series of questions are based on a type of ultrasound scan or an anatomical structure being scanned.

\*  \*  \*  \*  \*